United States Patent [19]

Savanuck

[11] Patent Number: 4,572,690
[45] Date of Patent: Feb. 25, 1986

[54] GRIPPING COMPOSITION DISPENSER AND GRIPPING COMPOSITION THEREFOR

[75] Inventor: Daniel F. Savanuck, Pikesville, Md.

[73] Assignee: Chemical Specialties Manufacturing Corporation, Baltimore, Md.

[21] Appl. No.: 576,715

[22] Filed: Feb. 3, 1984

[51] Int. Cl.⁴ ............................................. A44B 13/00
[52] U.S. Cl. .................................... 401/200; 424/64; 424/65; 424/69
[58] Field of Search ................. 401/200, 201; 424/65, 424/65, 69; 132/79 D, 82 R

[56] References Cited

U.S. PATENT DOCUMENTS

| | | | |
|---|---|---|---|
| 2,987,447 | 6/1961 | Ward | 424/69 |
| 3,193,869 | 7/1965 | Coppock, Jr. | 401/200 |
| 3,324,004 | 6/1967 | Nagler | 424/68 |
| 3,876,758 | 4/1975 | Beekman | 424/68 |
| 3,932,609 | 1/1976 | Rosenstreich et al. | 424/68 |
| 4,119,712 | 10/1978 | Goldner et al. | 424/69 |
| 4,365,184 | 12/1982 | Higton | 313/503 |
| 4,368,184 | 1/1983 | Drucker et al. | 401/200 |
| 4,448,560 | 5/1984 | Monaco, Jr. | 401/200 |

Primary Examiner—William R. Dixon, Jr.
Assistant Examiner—Margaret B. Medley
Attorney, Agent, or Firm—Leitner & Martin

[57] ABSTRACT

A rosin bag - type dispenser and a powder - form gripping composition therefor are disclosed. The gripping composition comprises a particular inorganic oxide in admixture with an astringent. The particulate inorganic oxide which is present as the major component of the admixture is suitably a low bulk density oxide such as fumed silica, alumina or titania. The astringent is preferably aluminum chlorohydrate.

24 Claims, 2 Drawing Figures

GRIPPING COMPOSITION DISPENSER AND GRIPPING COMPOSITION THEREFOR

BACKGROUND OF THE INVENTION

1. Field of the Invention

This invention relates to permeable, powder-containing dispensers generally used by athletes to maintain proper contact with hand-held objects such as gymnastic apparatuses, rackets, golf clubs, baseball bats, bowling balls, etc. Devices similar to those of the present invention are the well known "rosin bags".

2. Description of the Prior Art

Rosin bags which contain finely powdered rosin have long been used by pitchers in baseball. Permeable terry cloth bags such as disclosed in U.S. Pat. No. 3,193,869 employing diatomaceous earth have been shown to be useful to dry hands and achieve proper frictional engagement between hand and bowling ball.

Astringents and inorganic oxides have been used previously in antiperspirant powders as disclosed in U.S. Pat. No. 4,365,184; however, heretofor, it has never been recognized that such ingredients, when combined and used in the proportions and for the purpose of this invention, could provide a suitable rosin substitute which possessed both grip-enhancing/friction properties and permeability properties allowing dispensing through containers of the type used for rosin bags.

SUMMARY OF THE INVENTION

The present invention relates to the discovery that a powder comprising a minor proportion of astringent intimately admixed with a major proportion of a particulate friction-enhancing inorganic oxide can provide a viable rosin subsitute in permeable powder-containing dispensers, "rosin bags".

Although not wishing to be bound, it is believed that the astringent improves the friction-enhancing property of the oxides by ameliorating perspiration which is absorbed by and deactivates the friction-enhancing properties of such oxides—especially the low bulk density amorphous inorganic oxides which represent the most preferred form of oxides used in the invention.

One aspect of the present invention relates to a grip-enhancing material which is suitably retained in a rosin bag-type container for dispensing a grip-enchancing material. The material comprises a particulate inorganic oxide composition which provides friction when applied to a persons' hands in combination with an astringent composition.

The container suitably is a permeable container such as a bag. The inorganic oxide is preferably selected from the group consisting of fumed silica, fumed alumina, fumed titania and mixtures thereof. Any of the variety of astringents commonly used for human application such as in cosmetics are suitable for use in the invention. Most preferred is aluminum chlorohydrate. Fumed silica, which is both safe and readily available, is the preferred inorganic oxide.

The ratio by weight of fumed silica to aluminum chlorohydrate is preferably from about 20:1 to about 20:5 and most preferably the ratio by weight of fumed silica to aluminum chlorhydrate is about 8:1.

The most facile preparation comprises an intimate admixture of low bulk density inorganic oxide particles and astringent particles of higher density wherein the astringent particles are substantially smaller than the inorganic oxide particles. This, it is believed, allows for a plurality of smaller astringent particles to form around the inorganic oxide particles whereby the inorganic and astringent particles are maintained in admixed condition during storage and dispensing.

Also in accordance with the present invention the admixture is achieved by first impregnating the low bulk density inorganic oxide composition with a solution of astringent composition and thereafter removing the solvent.

It is desirable to achieve intimate admixture whereby grip-enhancing co-action of inorganic oxide and astringent is obtained.

DESCRIPTION OF THE PREFERRED EMBODIMENTS

Figure 1:
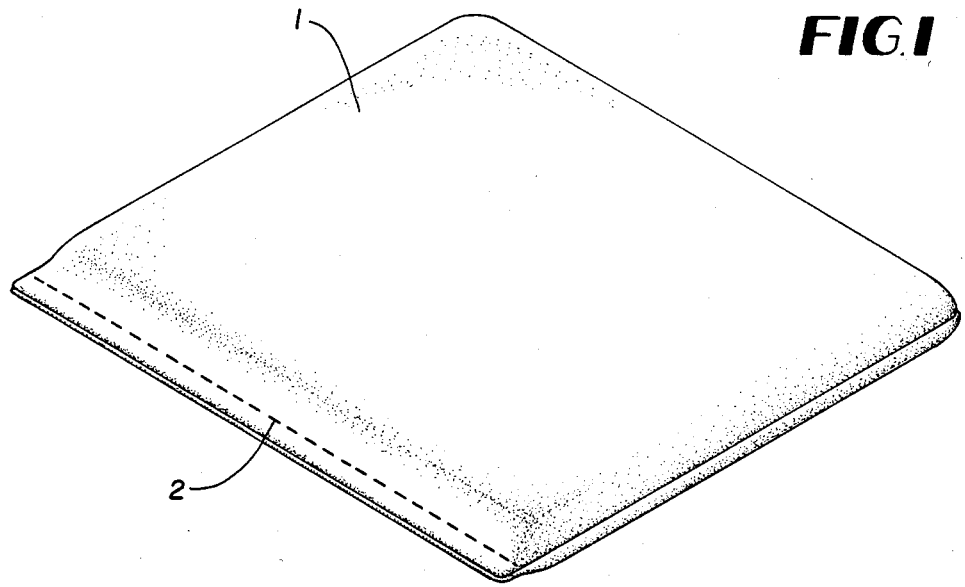
FIG. 1 represents a perspective view of a dispensing bag.

The present invention is perhaps best characterized as relating to a "rosin bag" in which a novel rosin substitute is incorporated.

Suitable inorganic oxides for use in the present invention are the low bulk density (high surface area) inorganic oxides such as fumed silicas manufactured by the Cab-O-Sil Division of Cabot Corporation and marketed under the trademark Cab-O-Sil. Cab-O-Sil is produced by the hydrolysis of silicon tetrachloride vapor in a flame of hydrogen and oxygen by which process an amorphous low bulk density fumed silica is formed having a bulk density of less than 0.1 gram per milliliter generally about 0.03 grams per milliliter. Other suitable fumed silicas are those sold by the Davison Chemical Division of Grace under the marks SYLOID and SYLOX. Generally low bulk density inorganic oxides have BET surface areas of about 20 $m^2/g$ or higher and bulk densities of less than about 10 lbs per cubic foot.

Also suitable as an inorganic oxide is Aluminum Oxide C, a fumed alumina produced by Degussa Inc., Teterboro, N.J. Such alumina has a bulk density of about 60 g/l and a BET surface area of about $100 \pm 15$ $m^2g$. Also suitable for use in the present invention is Titanum Dioxide P25, a fumed titania, likewise produced by Degussa which has a bulk density of about 80 g/l and a BET surface area of about $50 \pm 15$ $m^2/g$. The Degussa fumed alumina-containing compositions sold under the mark AEROSIL are also suitable for use in the present invention. Such amorphous aluminas have BET surface areas of from about 50 to about 380 $m^2/g$.

Of the plethora of astringents, ultrafine powdered astringents such aluminum chlorohydrate, $Al_2(OH)_5 \cdot 2 H_2O$, of smaller particle size than the low bulk density metal oxides with which they are combined, are preferred. By using astringent in ultrafine particulate form, initimate admixture of astringent and metal oxide is achieved and maintained by thorough mechanical mixing of the two components.

Preferably the content of astringent is form about 1% to about 25% by weight based on the inorganic oxide, most preferably about $10\% \pm 5\%$, of the admixture comprises astringent.

Where a porous bag is used, the porous bag is suitably selected to provide appropriate porosity such that the material is conveniently dispensed by manipulation of the bag. In accordance with the present invention, where the mixture used in an intimate admixture of 40 parts by weight, Cab-O-Sil fumed silica, and 5 parts by weight of super ultrafine aluminum chlorohydrate, a porous sythetic material such as Millspun II, manufactured by Millhiser Inc., Richmond, Va. is suitable for making the dispensing bag.

Though the size and content of the bag may vary as required, 4" by 4" bags containing about 5 grams of material have been found to represent a satisfactory size.

The bag, in turn, may be enclosed within a clear plastic envelope suitably of the zipper-type, which serves the further functions of protecting the contents from prolonged exposure and assuring the purchaser that the "rosin" in the bag has not been used/expelled. Other materials found suitable for dispensing bags are cotton, nylon and a DuPont material called TYVEK. The criteria for material selection as will immediately be appreciated is to ensure that the material is porous enough to allow a small amount of powder to cover the palm of the hand with minimum effort.

A suitable bag is illustrated by FIG. 1. The bag 1, may be constructed of any permeable material which serves to dispense the grip-enhancing contents. The bag after filling is sealed at the open end suitably by stitching along stitch line 2.

Figure 2:
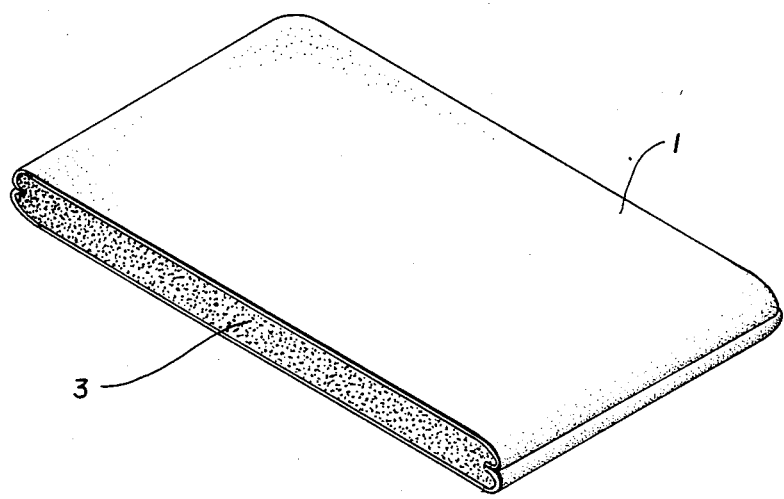
FIG. 2 represents a cut-away view of the bag illustrating the powder form, grip-enhancing material contained therein.

In FIG. 2, a cut-away view of bag 1, the bag and powdered contents 3 are illustrated.

Two suitable methods of making the admixture of the invention are described in the example which follows.

EXAMPLE

A first batch of intimately admixed low bulk density amorphous inorganic oxide and aluminum chlorohydrate astringent was prepared using the following procedure;

1. A 50% aqueous solution of aluminum chlorohydrate was formed.
2. 40 parts by weight of fumed silicon dioxide (Cab-O-Sil brand) were agitated in a high speed mixer.
3. 10 parts by weight of the 50% aqueous solution of aluminum chlorohydrate were added to the silicon dioxide while it was being agitated. Addition was effected by spraying the solution of of chlorohydrate into the blender containing the silicon oxide.
4. The impregnated silicon dioxide was thereafter dried to remove the water used as solvent for the aluminum chlorohydrate.

A second batch of intimately admixed low bulk density amorphous inorganic oxide and aluminum chlorohydrate astringent was prepared using the following procedure:

1. 40 parts by weight of fumed silcon dioxide (Cab-O-Sil brand Grade EH-5) and 5 parts by weight Super Ultrafine Aluminum Chorohydrate were placed in a mechanical blender. The aluminum chlorohydrate was obtained from the Rohets Chemical Company and contained about 85% particles of a size of less than 44 microns.
2. The two ingredients were physically mixed without addition of soluent to form a homogeneous admixture.

The first and second batch powder admixtures were placed in a permeable bag which was used to apply such powders as rosin substitutes to the hands of a bowler.

The powder operated satisfactorily to enhance the grip of the bowler.

When the cloth bag was squeezed in the palm of the hand an immediate drying of the hand occurred and friction was enhanced. The powder effluent from the bag need not be used as frequently as rosin or chalk because excessive perspiration is limited by the astringent component.

Results analogous to those in the foregoing example are achieved when other components described herein are substituated for those in the example. It is hence not intended to limit the invention to the details of the examples, but only broadly as defined in the following claims.

I claim:

1. A rosin bag-type device comprising:
   (a) a permeable container for dispensing a grip-enhancing material; and
   (b) an admixture within said permeable container, comprising a major portion by weight of a particulate friction enhancing inorganic oxide composition and a minor portion by weight of an astringent composition, said admixture being permeable through said container by manipulation of the container.

2. The device of claim 1 wherein the permeable container is a bag and the inorganic oxide is a low bulk density inorganic oxide selected from the group consisting of fumed silica, fumed alumina, fumed titania and mixtures thereof.

3. The device of claim 2 wherein the astringent is aluminum chlorohydrate.

4. The device of claim 2 wherein the low bulk density inorganic oxide is fumed silica.

5. The device of claim 4 wherein the astringent is aluminum chlorohydrate.

6. The device of claim 1 wherein the ratio by weight of fumed silica to aluminum chlorohydrate in from about 20:1 to about 20:5.

7. The device of claim 6 wherein the ratio by weight of fumed silica to aluminum chlorohydrate is about 8:1.

8. The device of claim 1 wherein the admixture comprises an intimate admixture of low bulk density inorganic oxide particles and astringent particles of higher density than the inorganic oxide particles, said astringent particles being of smaller size than said inorganic oxide particles to maintain said inorganic and astringent particles in admixed condition during storage and dispensing.

9. The device of claim 2 wherein the admixture comprises an intimate admixture of low bulk density inorganic oxide particles and astringent particles of higher density than the inorganic oxide particles, said astringent particles being of smaller size than said inorganic oxide particles to maintain said inorganic and astringent particles in admixed condition during storage and dispensing.

10. The device of claim 3 wherein the admixture comprises an intimate admixture of low bulk density inorganic oxide particles and astringent particles of higher density than the inorganic oxide particles, said astringent particles being of smaller size than said inorganic oxide particles to maintain said inorganic and astringent particles in admixed condition during storage and dispensing.

11. The device of claim 4 wherein the admixture comprises an intimate admixture of low bulk density inorganic oxide particles and astringent particles of higher density than the inorganic oxide particles, said astringent particles being of smaller size than said inorganic oxide particles to maintain said inorganic and astringent particles in admixed condition during storage and dispensing.

12. The device of claim 5 wherein the admixture comprises an intimate admixture of low bulk density inorganic oxide particles and astringent particles of higher density than the inorganic oxide particles, said astringent particles being of smaller size than said inorganic oxide particles to maintain said inorganic and astringent particles in admixed condition during storage and dispensing.

13. The device of claim 6 wherein the admixture comprises an intimate admixture of low bulk density inorganic oxide particles and astringent particles of higher density than the inorganic oxide particles, said astringent particles being of smaller size than said inorganic oxide particles to mantain said inorganic and astringent particles in admixed condition during storage and dispensing.

14. The device of claim 7 wherein the admixture comprises an intimate admixture of low bulk density inorganic oxide particles and astringent particles of higher density than the inorganic oxide particles, said astringent particles being of smaller size than said inorganic oxide particles to maintain said inorganic and astringent particles in admixed condition during storage and dispensing.

15. The device of claim 1 wherein the admixture comprises a low bulk density inorganic oxide composition having impregnated thereon an astringent composition.

16. The device of claim 5 wherein the admixture comprises a low bulk density inorganic oxide composition having impregnated thereon an astringent composition.

17. The device of claim 8 wherein the admixture comprises a low bulk density inorganic oxide composition having impregnated thereon an astringent composition.

18. A hand-grip enhancing powder comprising, in admixture, a major portion by weight of a friction enhancing particulate inorganic oxide and a minor portion by weight of an astringent compositon.

19. The powder of claim 18 wherein the inorganic oxide is a low bulk density inorganic oxide selected from the group consisting of fumed silica, fumed alumina, fumed titania and mixtures thereof.

20. The powder of claim 19 wherein the astringent is aluminum chlorohydrate.

21. The powder of claim 19 wherein the low bulk density inorganic oxide is fumed silica.

22. The powder of claim 21 wherein the astringent is aluminum chlorohydrate.

23. The powder of claim 1 wherein the ratio by weight of fumed silica to aluminum chlorohydrate in from about 20:1 to about 20:5.

24. The powder of claim 23 wherein the ratio by weight of fumed silica to aluminum chlorhydrate is about 8:1.

* * * * *